United States Patent [19]

Morgan

[11] E Re. 28,873

[45] Reissued June 22, 1976

[54] SCLERAL LENS WITH ATTACHED TUBE

[76] Inventor: Loran B. Morgan, 138 Linda Vista, Torrington, Wyo. 82240

[22] Filed: May 13, 1974

[21] Appl. No.: 469,414

Related U.S. Patent Documents

Reissue of:

[64] Patent No.: 3,664,340
Issued: May 23, 1972
Appl. No.: 867,198
Filed: Oct. 17, 1969

[52] U.S. Cl. ..... 128/249
[51] Int. Cl.[2] ..... A61M 7/00
[58] Field of Search ..... 128/249, 248, 227, 260

[56] References Cited

UNITED STATES PATENTS

| | | | |
|---|---|---|---|
| 1,548,780 | 8/1925 | Herbert | 351/9 |
| 2,347,488 | 4/1944 | Lawlor et al. | 128/260 X |
| 3,302,646 | 2/1967 | Behney | 128/249 X |
| 3,392,725 | 7/1968 | Behney | 128/249 |

FOREIGN PATENTS OR APPLICATIONS

| | | | |
|---|---|---|---|
| 435,542 | 3/1912 | France | 128/249 |
| 692,146 | 10/1930 | France | 128/249 |
| 332,341 | 1/1921 | Germany | 128/249 |
| 125,795 | 5/1919 | United Kingdom | 128/249 |
| 923,977 | 4/1963 | United Kingdom | 128/249 |

*Primary Examiner*—John D. Yasko
*Attorney, Agent, or Firm*—Sheridan, Ross & Fields

[57] ABSTRACT

Means for scientifically supervised use when treating severe injuries and infections of the human eye. It enables a doctor or his nurse to administer a regulable but constant instillation of an antibiotic solution, chemotherapeutic agents, steroids or like solutions to the corneal area of the eyeball. A molded shield is conformingly superimposed on the eyeball and embodies a centralized concavo-convex corneal lens surrounded by a rim-like annulus which resides conformingly atop the sclera. Flexible tubing delivers the solution from a solution feeding bottle to the annulus in a manner that the eyeball is continuously lavaged while the over-all shield "floats" atop the constantly existing film of fluid.

4 Claims, 3 Drawing Figures

Loran B. Morgan
INVENTOR.

BY Clarence A. O'Brien and Harvey B. Jacobson
Attorneys

SCLERAL LENS WITH ATTACHED TUBE

Matter enclosed in heavy brackets [ ] appears in the original patent but forms no part of this reissue specification; matter printed in italics indicates the additions made by reissue.

This invention relates to special purpose eye shields and applicators such as are scientifically designed and expressly adapted for supervised use and has to do, more particularly, with means which enables the doctor or trained nurse to achieve the results desired while pursuing the procedures followed in the currently accepted practices of treating severe injuries and troublesome eye infections.

One of the two most widely accepted modes of treatment involves fitting of a flush scleral lens in a manner to promote epithelization and to relieve pain which is attributable to passage of the eyelids over an ulcerated cornea. The other accepted procedure is the constant instillation of antibiotic, chemotherapeutic agents, steroids and the like by perforating the lower eyelid and inserting the discharge end of a prerequisite polyethylene solution delivering tube. The herein disclosed concept invokes the use of a molded cup-like eye shield of conformable configuration and which has an attached flexible polyethylene tube or hose which achieves the combined therapy but without surgical procedures. Continuous medication is carried out with the aid of a suitably constructed and suspended and controlled solution bottle and tube carried thereby and communicatively connectible to the aforementioned tube.

Briefly the over-all concept has to do with the tube-equipped eye shield, the suspended solution containing bottle, and the clip-controlled tube which leads from the gravity feeding end of the bottle to the intake end of the first-named tube. The eye shield is of one piece precision-molded plastic or equivalent material. This shield is of cup-like form and is conformably designed and adapted to fit upon the selected surface of the patient's eyeball between said surface and the overlying eyelids. More explicitly, the shield embodies an endless annular rim portion which is superimposed upon and coordinates with the sclera and centralized apical portion providing a corneal lens. The remote controllable source of supply of the prescribed medicated solution is preferably in the form of a somewhat conventional type valved fluid containing gravity feeding suspended bottle. Elongated flexible tubing of requisite length, cross-section and material and preferably sectional has an intake end communicatively joined to the discharge end of the bottle and with its other end communicatively joined to the rim portion of the shield whereby the eyeball can be continuously lavaged while the over-all shield is caused to float on the constantly existing film of fluid between the eyeball and shield.

To the ends desired and in carrying out the preferred embodiment of the invention the tubing embodies a first length of plastic tubing carried by and forming a companion integral part of the eye shield. In addition, there is a second length of tubing which is carried by the source of supply, that is, the aforementioned bottle. Then, too, coupling and adapter means is carried by the free intake end of the first length of tubing and has a socket member for separable telescoping connection of the free discharge end of the second length of tubing.

Persons conversant with the field of invention are aware that eye shields of one type or another for medicament and solution applying and irrigating eye treatments are not broadly new. For background purposes and as generally exemplary of the state of the art to which the invention relates, the reader may refer to the eye treating appliance in a U.S. Patent issued to Charles A. Behney, No. 3,302,646 which provides treatment and protection for an inflamed eye but which lacks the control of the medication in that an amount of the medicament is contained within the lens when it is placed upon the eyeball. In fact, the Behney invention involves the application of ointment to the eye and a pocket containing the ointment in a confined state. The present invention by contrast has to do with a continuous drip of completely scientifically controlled medication confined to the corneal area of the eyeball. This dose may be increased, decreased, varied by the hour or stopped at any time. In addition a substantial amount of comfort is given to the patient by the fact that the eyeball is being continuously lavaged and the lens actually assumes a floating state on the eye rather than being confined directly to and contacting the eyeball. Considerable advantage is attached to the face that the lens floats upon the cornea and is not tightly sealed in its given position. Then, too, one of the main features of the present invention is the use of the same for sterilizing the eye as a step previous to surgery. It follows that the instant invention well serves the specific purposes for which it has been devised and successfully used.

These together with other objects and advantages which will become subsequently apparent reside in the details of construction and operation as more fully hereinafter described and claimed, reference being had to the accompanying drawings forming a part hereof, wherein like numerals refer to like parts throughout, and in which:

Figure 3:
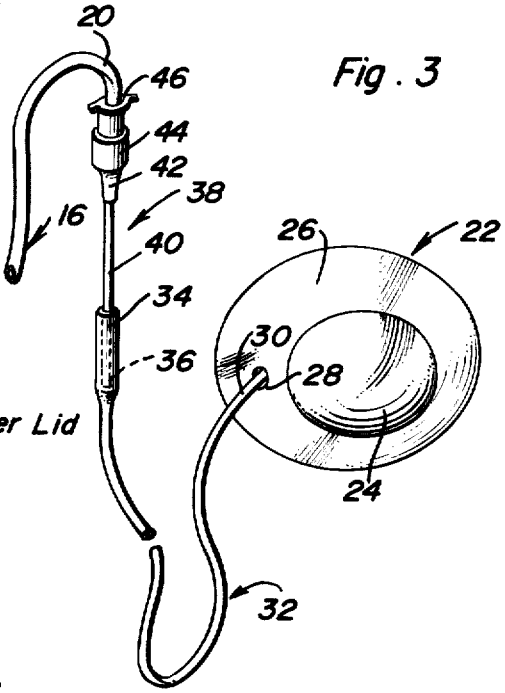

And FIG. 3 is a view in perspective emphasizing the construction of the eye shield and specially constructed tube means which is operatively connected thereto.

Figure 1:
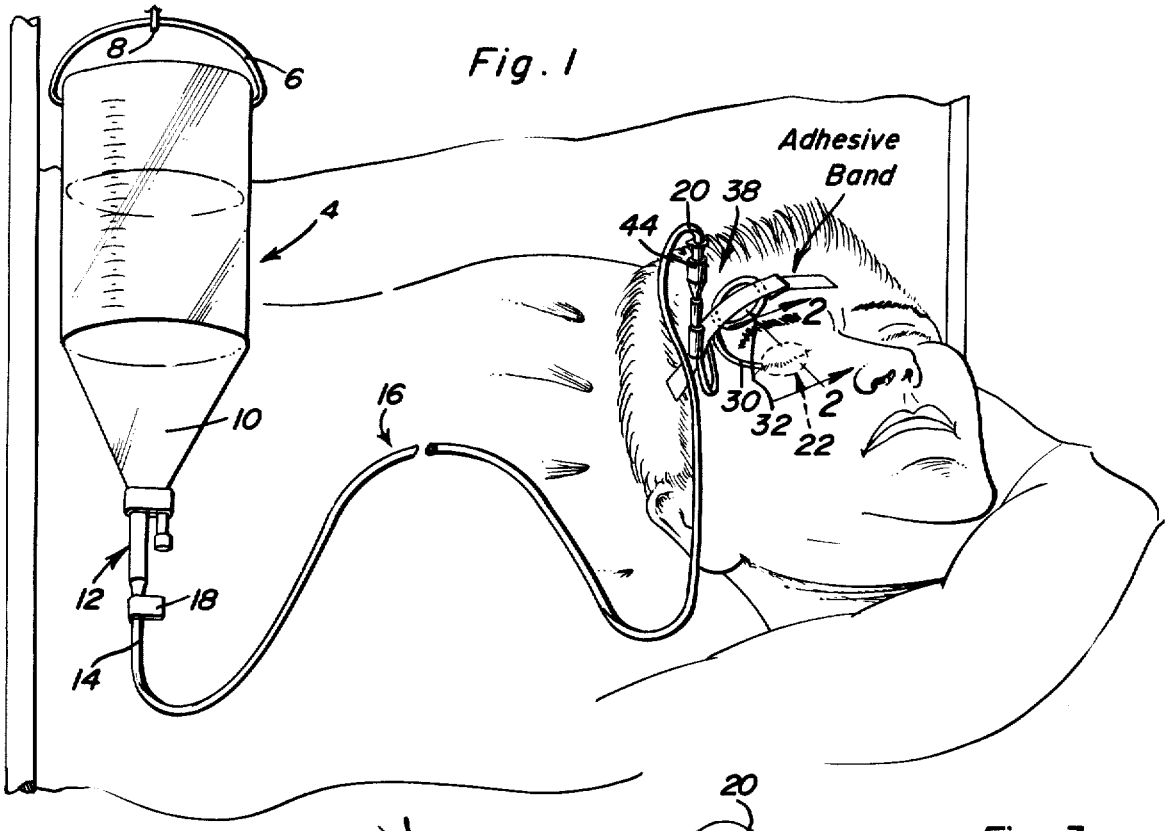
FIG. 1 is a view in perspective showing the over-all combination, that is the suspended solution containing and controlling bottle at the left, the eye shield in usable position at the right and the tube means with one tube connected to and leading from the bottle and the other tube connected to the eye shield and with adjacent ends of the tubes coupled together.
Figure 2:
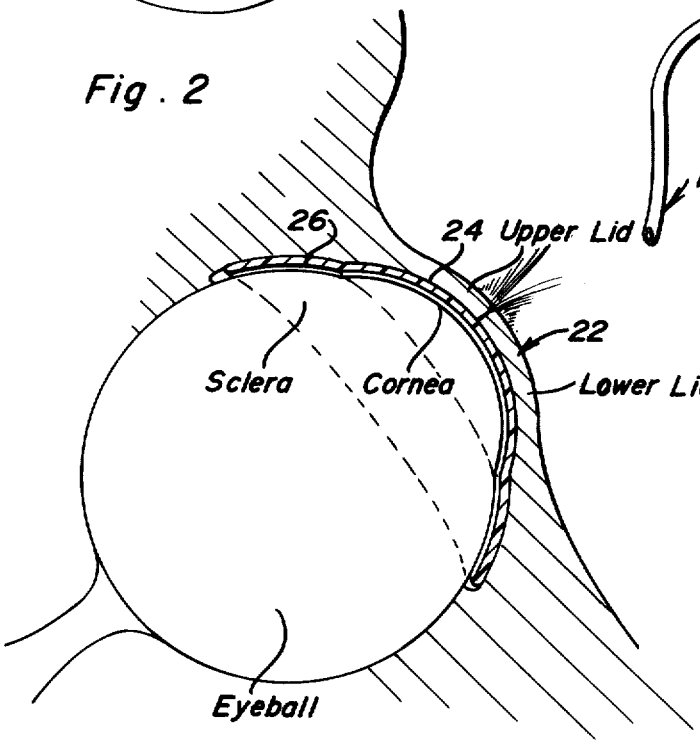
FIG. 2 is an enlarged detail section taken approximately on the plane of the section line 2—2 of FIG. 1, looking in the direction of the indicating arrows.

With reference to FIG. 1 the aforementioned source of supply comprises an appropriately constructed and gauged solution containing bottle 4 which has a supporting bail 6 suspended from the ceiling or other support means as at 8. The lower funneling end 10 is provided with valve means 12 to which an end portion 14 of the delivery hole or tubing 16 is connected. The numeral 18 designates the usual clip which is employed at will for permitting the flow or cutting the flow off in a generally well known manner. The discharge end of this hose or tubing is denoted at 20.

The essence of the invention has to do, broadly stated, with the insertable and removable precision molded cup-shaped applicator or eye shield 22. This component comprises a one piece unit which is characerized by a concavo-convex cornea lens 24 of requisite iameter and convexity. This lens is encompassed or urrounded by an endless concavo-convex part which is ere referred to as a comformable rim 26. The rim is rovided on one side with an opening 28 for the atached delivery end 30 of the polyethylene tubing 32. his tubing or tube is of requisite length and cross-secion and has its intake end 34 fitted over one end of a igid needle-like tube 36 which constitutes an adapter 8. The needle-like member itself is denoted at 40 and as its upper end joined as at 42 to the lower end of an longated cup-like coupling member 44 having an apropriate adapter socket 46 for the insertable and renovable communicating end 20 of the aforementioned upply tube 16.

It will be evident to the reader that the shield 22 is actually similar to a contact lens molded to fit the eyeball but floating on it by reason of the constant applicaion of fluid or other medication through the tube neans and accordingly unlike either a plain fountain or cup type applicator such as is used in prior art irrigating appliances. It follows that the floating effect is stressed n that there is no direct actual contact of the shield or ens means 22 with the eyeball.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. Means for scientifically supervised use when the user is called upon to administer a manually controlled but a constant instillation of an antibiotic, chemotherapeutic agent, steroid or a like medicated solution to and for confining the same to the corneal area of a patient's eyeball comprising: a one piece precision-molded cup-like eye shield designed and adapted to be conformingly fitted upon exterior surface portions of a patient's eyeball between said surface and the coacting eyelids, said shield embodying a centralized concavo-convex lens which is registrable with and is adapted to conformingly span the cornea of the eyeball, and also embodying an annular concave rim portion marginally encompassing said lens and adapted to conformingly overlie the sclera of said eyeball, a prescribed length of flexible tubing having one end communicatively connected to an intake orifice provided in a predetermined portion of said shield and its opposite end free for coordinating communication with a discharge end of a second length of tubing which is adapted to supply a medicated solution from a suitable source of supply, said free end being provided with an adapter, said adapter comprising a rigid hollow needle-like stem open at its ends, one open end being fitted communicatively into the bore of said free end, the other open end having a communicating socket member, said socket member being designed and adapted to receive the aforementioned discharge end.

*2. Apparatus for administering a continuously flowing supply of a liquid medicated solution to at least the corneal portion of a patient's eyeball, comprising:*

*a cup-like eye shield having a concave inner face of predetermined size and shape to overlie the frontal portion of the eyeball and having a smooth peripheral margin adapted to initially engage corresponding marginal portions of the eyeball;*

*the outer surface of the shield being adapted to contact the inner surfaces of the eyelids and maintain them separated from the eyeball;*

*the shield being provided with an inlet port extending therethrough to define a flow path for entry of liquid between the shield and the eyeball;*

*a length of flexible tubing having one end connected with the inlet port and an opposite end free for connection to the discharge end of a second length of tubing which is adapted to supply a medicated liquid from a suitable source of supply;*

*said free end being provided with an adapter; and*

*said adapter comprising a rigid hollow needle-like stem open at its ends, one open end being fitted communicatively into the bore of said free end, the other open end having a communicating socket member, said socket member being designed and adapted to receive the aforementioned discharge end.*

*3. A method of administering a continuously flowing supply of a liquid medicated solution to at least the corneal portion of a patient's eyeball, comprising:*

*providing a cup-like eye shield having only an inlet port therethrough and otherwise being imperforate and having a concave inner face with a smooth peripheral margin;*

*positioning the shield between the eyeball and the eyelids with the inner face overlying the frontal portion of the eyeball and with at least the margin releasably engaging corresponding marginal portions of the eyeball and with the outer face in contact with the inner surfaces of the eyelids to maintain them out of engagement with the eyeball;*

*transmitting medicated liquid through the inlet port to the inner face of the shield and the eyeball; and*

*continuously applying hydraulic pressure to the liquid over a prolonged period of time at a pressure level sufficient to force the margin out of contact with the eyeball and maintain a continuous flow of liquid over substantially the entire surface of the eyeball and out between the eyeball and the margin of the shield.*

*4. A method as claimed in claim 3, further including:*

*placing the patient in a generally prone attitude facing upward so that the liquid flows more uniformly over the eyeball;*

*providing a reservoir containing the medicated liquid;*

*connecting the reservoir to the inlet port with a length of tubing; and*

*supporting the reservoir at a level above the patient sufficient to produce by gravity the amount of hydraulic pressure necessary to initiate and maintain the flow of liquid between the eyeball and the shield and out between the eyeball and the peripheral margin of the shield.*

* * * * *